(12) United States Patent
Knight et al.

(10) Patent No.: US 9,007,466 B2
(45) Date of Patent: Apr. 14, 2015

(54) SYSTEM AND METHOD FOR THERMOGRAPHIC INSPECTION

(75) Inventors: Bryon Edward Knight, Ballston Lake, NY (US); Donald Robert Howard, Troy, NY (US); Harry Israel Ringermacher, Delanson, NY (US)

(73) Assignee: General Electric Company, Niskayuna, NY (US)

( * ) Notice: Subject to any disclaimer, the term of this patent is extended or adjusted under 35 U.S.C. 154(b) by 271 days.

(21) Appl. No.: 13/094,921

(22) Filed: Apr. 27, 2011

(65) Prior Publication Data

US 2012/0274778 A1 Nov. 1, 2012

(51) Int. Cl.
*H04N 5/33* (2006.01)
*G01N 25/72* (2006.01)
*G01N 25/00* (2006.01)

(52) U.S. Cl.
CPC ............... *G01N 25/72* (2013.01); *G01N 25/00* (2013.01); *H04N 5/332* (2013.01); *H04N 5/33* (2013.01)

(58) Field of Classification Search
CPC ......... G01N 25/72; G01N 25/00; H04N 5/33; H04N 5/332
USPC ............ 250/332, 330; 348/164, 166; 382/154
See application file for complete search history.

(56) References Cited

U.S. PATENT DOCUMENTS

| | | | |
|---|---|---|---|
| 5,711,603 A | | 1/1998 | Ringermacher et al. |
| 6,065,072 A * | | 5/2000 | Flath ............................. 710/29 |
| 6,367,968 B1 * | | 4/2002 | Ringermacher et al. .......... 374/7 |
| 6,367,969 B1 * | | 4/2002 | Ringermacher et al. .......... 374/7 |
| 6,394,646 B1 * | | 5/2002 | Ringermacher et al. .......... 374/7 |
| 7,365,330 B1 | | 4/2008 | Sun |
| 7,408,156 B2 * | | 8/2008 | Yannacone et al. ............ 250/332 |
| 7,516,663 B2 | | 4/2009 | Ringermacher et al. |
| 7,724,925 B2 * | | 5/2010 | Shepard ......................... 382/115 |
| 7,822,268 B2 | | 10/2010 | Rothenfusser et al. |
| 7,966,883 B2 * | | 6/2011 | Lorraine et al. ................. 73/601 |
| 2004/0041096 A1 | | 3/2004 | Sun et al. |
| 2012/0013745 A1 * | | 1/2012 | Kang et al. ..................... 348/164 |
| 2012/0019622 A1 * | | 1/2012 | Rousselle et al. ................ 348/46 |

FOREIGN PATENT DOCUMENTS

| | | |
|---|---|---|
| EP | 1918698 A1 | 5/2008 |
| WO | 0063642 A1 | 10/2000 |
| WO | 0141421 A2 | 6/2001 |

OTHER PUBLICATIONS

Search Report and Written Opinion from corresponding EP Application No. 12165067.5-1240 dated Sep. 5, 2012.

* cited by examiner

*Primary Examiner* — Christopher S Kelley
*Assistant Examiner* — Zhihan Zhou
(74) *Attorney, Agent, or Firm* — Ann M. Agosti

(57) ABSTRACT

A method for thermographic imaging is described. The method captures a plurality of thermal images of a surface of an object, at non-linear intervals over a period of time, each of the thermal images being associated with temporal data. The method then processes the plurality of thermal images and the temporal data, and identifies features within the object based on the processing.

19 Claims, 3 Drawing Sheets

SYSTEM AND METHOD FOR THERMOGRAPHIC INSPECTION

BACKGROUND

Embodiments presented herein relate generally to infra-red imaging, and more specifically to transient thermographic inspection.

Thermographic inspection is the nondestructive testing of objects through imaging of thermal patterns on the object's surface. Thermographic inspection is often preferred to other nondestructive testing techniques such as ultrasonic inspection and radiographic inspection, for various advantages offered by thermographic inspection. Thermographic inspection is non-contact, non-intrusive, allows for detection of subsurface detects close to the surface, allows for inspection of large surfaces, and offers high speed inspection. One form of thermographic inspection is transient thermography. Transient thermography involves observing the temperature distribution on the surface of an object under test as it is subjected to a thermal transient such as a pulse of heat or a pulse of heat sink, and then allowed to return to ambient temperature. Any flaws present are detected as abnormalities in the surface temperature distribution during this thermal transient. Transient thermography is particularly well suited to the inspection of composite materials. The relatively low thermal conductivity of composite materials results in relatively long-lived thermal transients, therefore making the thermal transient easy to detect with a thermal camera.

Some known thermographic inspection techniques are operator dependent techniques, involving an operator to watch a thermal video of the object under test. The operator then observes the video for changes in contrast caused due to flaws within the object. Such techniques are skill intensive and require much manual effort. Automated thermographic inspection techniques also exist. Automated thermographic inspection uses a heat source such as a high intensity flash lamp to heat the surface of an object under test. An infra-red camera then takes a series of thermal images or thermograms of the object under test. The images are then post processed to identify features in the object under test.

Known automated thermographic inspection techniques use an infra-red camera driven at a constant frame rate. In other words, the infra-red camera is adapted to capture thermal images at fixed intervals of time. However, the thermal activity occurs at a non-linear rate. This causes too few thermal images being captured at the beginning of the thermal transient, when the thermal activity is high, and too many thermal images (with a large proportion being redundant images) being captured at the end of the thermal transient when the thermal activity is significantly slower. This causes very large data files that require a large buffer memory, a faster bus, and subsequently requires large disk space for storage and archival. These higher computing requirements increase the cost of the thermographic inspection system. Some techniques may partly address the storage problem by extracting thermal images from the large set of captured images. However, such techniques still require large buffers and fast busses to facilitate high speed image capture.

Therefore, there is a need for a thermographic inspection system that addresses these and other shortcomings associated with known solutions.

BRIEF DESCRIPTION

A method for thermographic imaging is described. The method captures a plurality of thermal images of a surface of an object at non-linear intervals over a period of time, each of the thermal images being associated with temporal data. The method further includes processing the plurality of thermal images and the temporal data, and identifying features within the object based on the processing.

A system for thermographic imaging is described. The system includes an infra-red imaging device that captures a plurality of thermal images of a surface of an object. The system further includes a variable time base generator that triggers the infra-red imaging device at non-linear intervals over a period of time. The system further includes a time module that associates temporal data with each of the plurality of thermal images. In some embodiments, the system may also include a processor for processing the plurality of thermal images taking into account the temporal data associated with each of the plurality of thermal images, and identifying features within the object. In some further embodiments, the system may also include a heater for heating the surface of the object.

DETAILED DESCRIPTION

Embodiments of a thermographic imaging system are presented herein. The system employs a non-linear time base for triggering an infra red (IR) camera, to enable imaging at a non-linear rate. In transient thermographic testing, for example, the object under test is heated by a predefined temperature. Heating is then stopped and the object under test allowed to return to ambient temperature. During the thermal transient, thermal activity of the object under test takes place at a non-linear rate dependant on various factors such as, but not limited to, emissivity, absorptivity, reflectivity, and temperature of the object under test. Specifically, the thermal activity occurs rapidly at the beginning of the thermal transient, and slows down as the thermal transient progresses. Thus, imaging at the non-linear rate may reduce the number of redundant images, thus reducing requirements of processing power, buffer memory, and image file sizes. The system stores temporal data associated with each of the captured images for further processing. In some embodiments, the system also includes a processing module for detecting and identifying features in an object under test.

Figure 1:
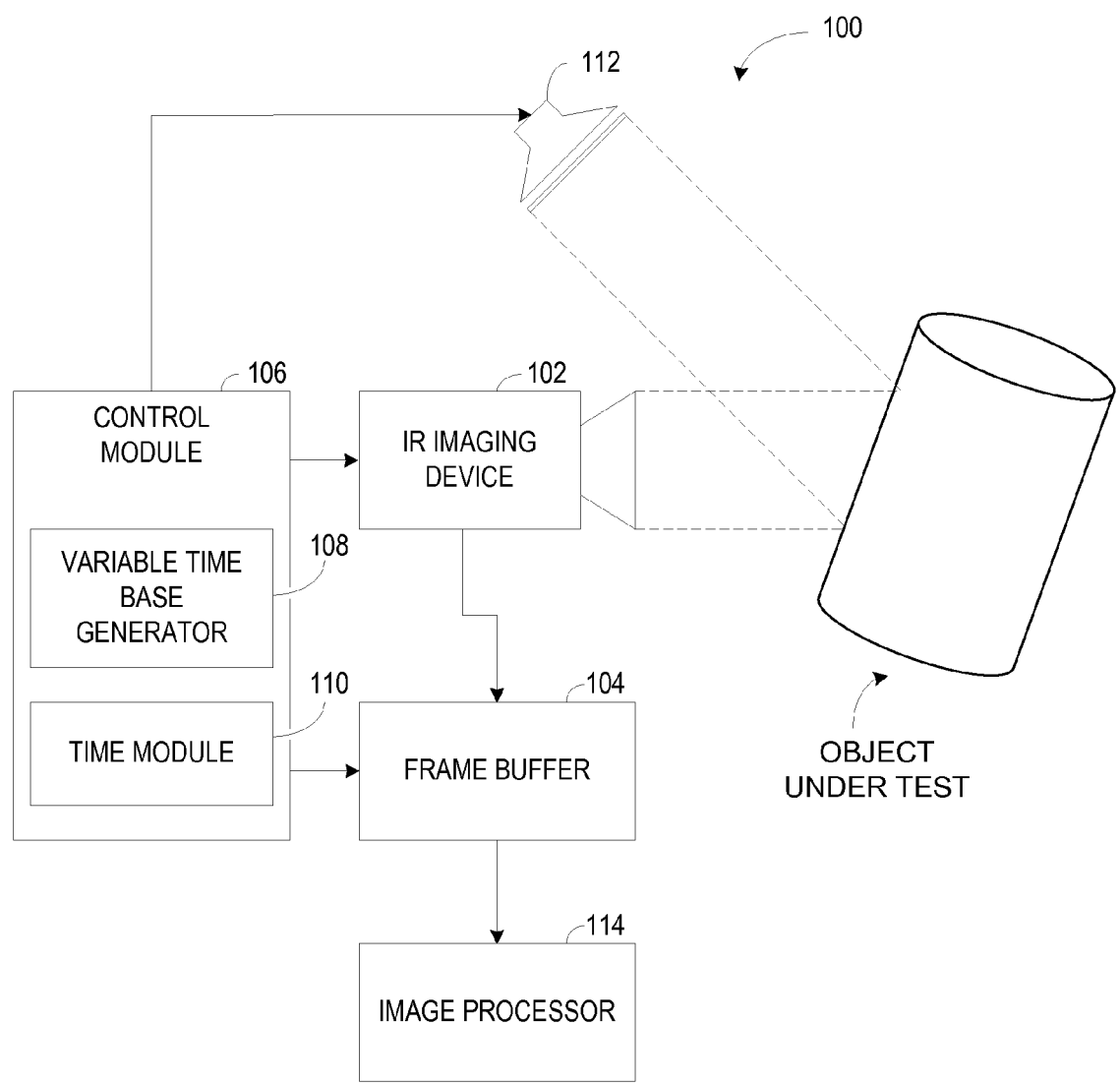
FIG. 1 is a simplified block diagram of an example thermographic inspection system, according to one embodiment.

FIG. 1 illustrates a simplified block diagram of an example thermographic imaging system 100, according to various embodiments. The thermographic imaging system 100 includes an IR imaging device 102, a frame buffer 104, and a control module 106. The control module 106 further includes a variable time base generator 108, and a time module 110. The thermographic imaging system 100 may include a heater 112, and an image processor 114. However, the heater 112, and the image processor 114 may be part of other equipment used for thermographic inspection and analysis. The heater 112 may include a high intensity discharge tube flash unit, a continuous infrared lamp, an induction heating unit, an ultrasonic vibration heater, or the like.

The IR imaging device 102 may include an IR sensor such as, but not limited to, a focal plane array IR sensor. The IR sensor may be, for example, a vanadium oxide microbolometer array. It should be appreciated that other IR sensors may also be used. The IR imaging device 102 may further include one or more IR lenses to produce a sharp image on the IR sensor. The IR lens may be designed to pass only light in the infra red spectrum.

The frame buffer 104 temporarily stores the thermal images captured by the IR imaging device 102, until the thermal images can be transferred to a non-volatile storage device, or transmitted over a network to an image processing terminal. The frame buffer 104 may be a high speed semiconductor memory device.

The control module 106 controls the operation of the IR imaging device 102, and the frame buffer 104. The control module 106 includes the variable time base generator 108, and the time module 110. The variable time base generator 108 generates a non-linear time base signal for triggering the IR imaging device 102. The non-linear time base signal triggers the IR imaging device 102 at non-linear intervals of time. In other words, the variable time base generator 108 causes the frame rate of the IR imaging device 102 to change over time. In various implementations, the variable time base generator 108 triggers the IR imaging device 102 after short time intervals at the beginning of a thermal transient, where a noticeable difference in thermal activity occurs in a short time interval. As the thermal transient progresses, the variable time base generator 108 triggers the IR imaging device 102 after longer time intervals, since a difference in thermal activity may only be noticed at much longer time intervals. Thus, the use of a non-linear time base signal enables capturing an optimal number of thermal images and reducing the number of redundant thermal images.

Figure 2:
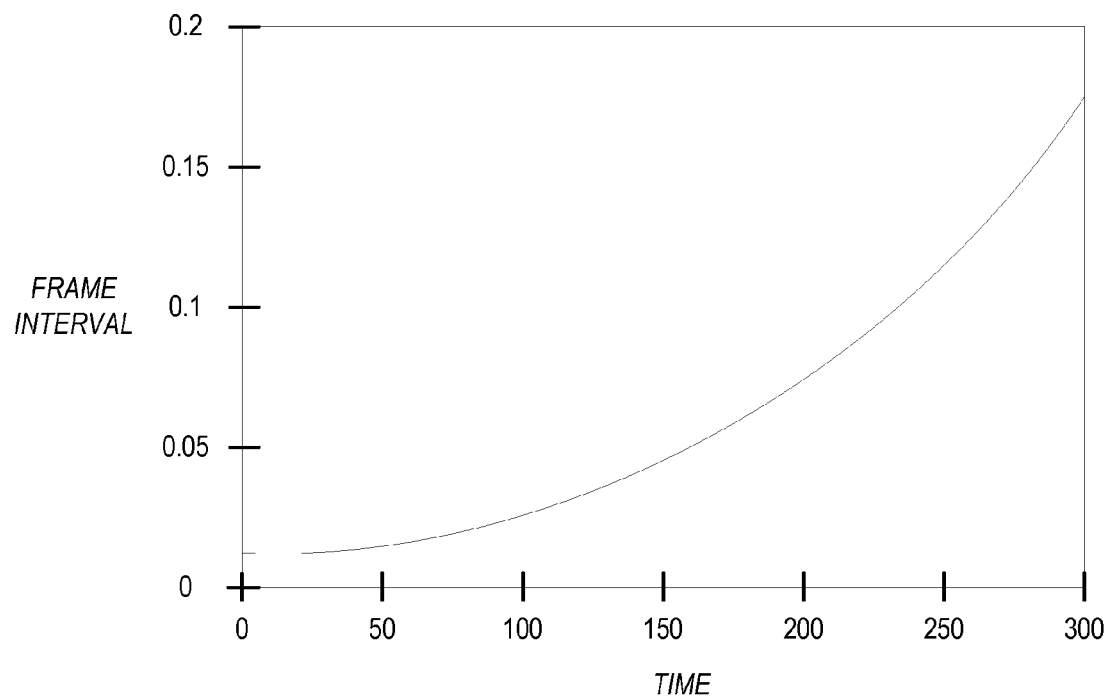
FIG. 2 is an example time-base function used for the thermographic inspection system, according to one embodiment.
Figure 3:
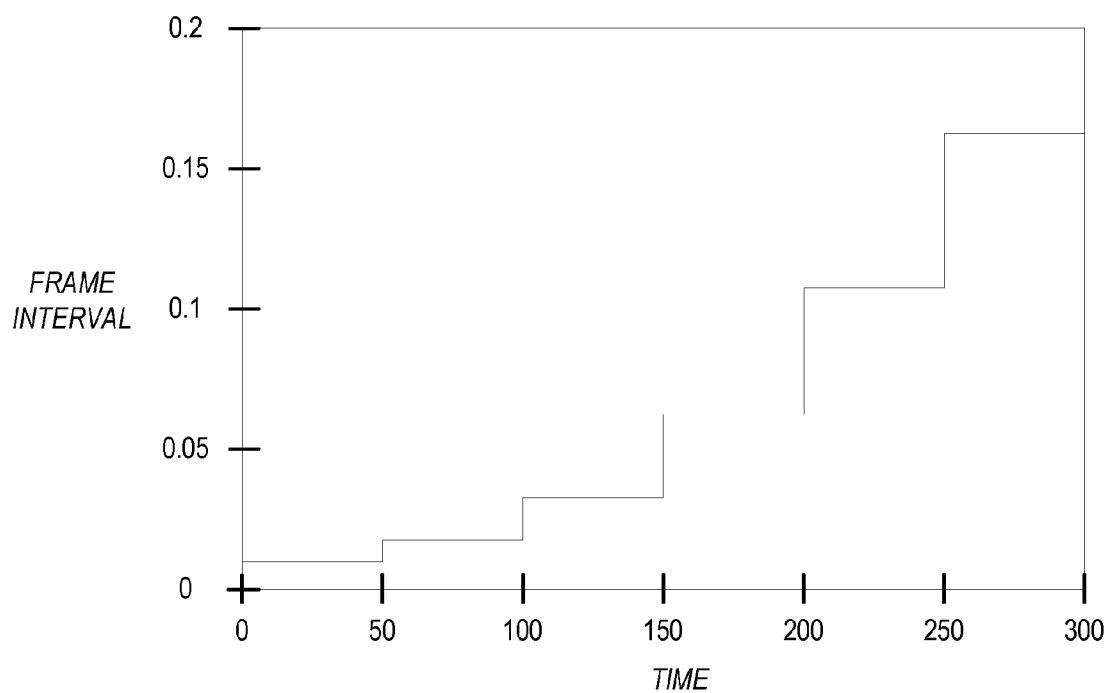
FIG. 3 is an example time-base function used for the thermographic inspection system, according to another embodiment.

The variable time base generator 108 may generate a continuously varying time base signal to trigger the IR imaging device 102. FIG. 2 illustrates an example time base signal that varies continuously with time. Alternatively, the variable time base generator 108 may generate a discretely varying time base signal, such as a step function of time. FIG. 3 illustrates an example time base signal that varies as a step function of time. In one implementation, the time base function of the variable time base generator 108 may be designed to complement the rate of thermal activity. In another implementation, the time base function of the variable time base generator 108 may be designed to complement an image processing operation of the image processor 114. For instance, the time base function may be designed to complement a Gaussian function for temporal smoothing of the series of captured thermal images.

The variable time base generator 108 may be implemented as an analog circuit using, for example, square law devices such as MOSFETs operating in the saturation region, capacitors for exponential time base, operational amplifiers and so forth. Alternatively, the variable time base generator 108 may be implemented as a digital circuit using, for example, a microprocessor, a programmable logic device such as a field programmable gate array, and so forth. In one example implementation, a microprocessor may be programmed with a time base computing function, to generate the variable time base signal.

In some low complexity thermal imaging systems, the variable time base generator 108 may be hardcoded or hardwired into the thermal imaging system 100. Such an implementation may be suitable for low cost thermal imaging systems and portable thermal imaging systems. Alternatively, the variable time base generator 108 may be a programmable or configurable time base generator. One example implementation of a programmable variable time base generator may accept user input of a time base function. In another example implementation, the programmable variable time base generator may have stored thereon in a memory, a plurality of time base functions. The programmable variable time base generator may accept user selection of one of the plurality of time base functions. Each of the plurality of time base functions may be associated with a specific type of object to be tested, or for specific materials, or for specific physical dimensions. Such a system may accept inputs to select the specific type of object to be tested, or the specific material, or the specific physical dimensions, or a combination thereof, and select a suitable time base function based on the input.

The control module 106 also includes a time module 110. The time module 110 generates temporal data for each of the captured thermal images. The temporal data may be an accurate time stamp precise to a millisecond, for example. The temporal data may then be used for processing the thermal images. In one implementation, the time module 110 stores the generated temporal data in the frame buffer 104, in association with the appropriate thermal image. The control module 106 may be configured to precisely synchronize the transfer of the thermal image captured by the IR imaging device 102 into the frame buffer 104, with the transfer of the temporal data from the time stamping module 110 to the frame buffer 104.

The image processor 114 then processes the thermal images stored in the frame buffer 104 to identify features within the object under test. The image processor 114 may use any suitable algorithm for processing the thermal images. However, the image processor 114 may now directly use the temporal data associated the thermal images to identify features, instead of the conventional technique of using frame numbers translated into an estimated time of thermal image capture.

Figure 4:
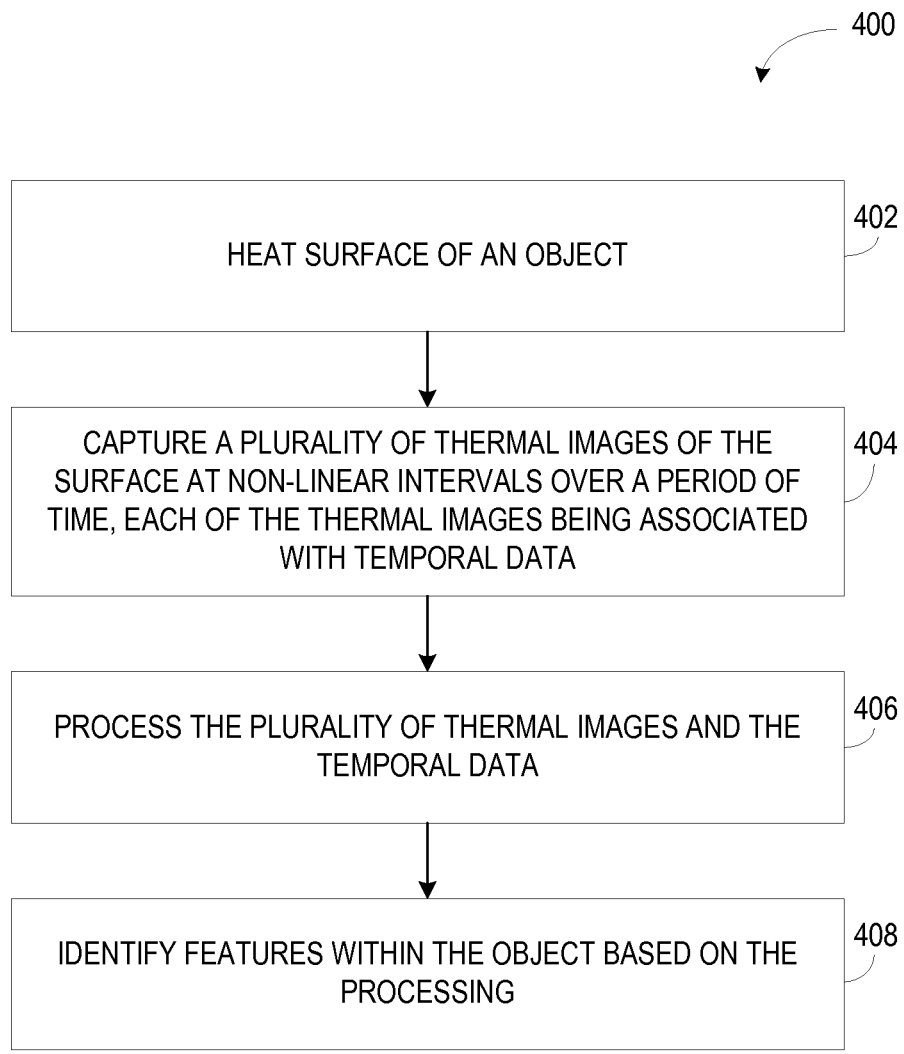
FIG. 4 is a flowchart of an example process of thermographic analysis, according to one embodiment.

FIG. 4 is a flowchart illustrating an example process of thermal imaging, according to one embodiment. At step 402, heater 112 heats a surface of the object under test. The heater 112 may directly heat the surface by "illuminating" the surface by infrared energy using, for example, a high intensity discharge tube flash, or a continuous heat wave. Alternatively, the heater 112 may indirectly heat the surface by subjecting other parts of the object under test to energy, thus causing heating of the surface. Such indirect heating may be effected using, for example, inductive heating, or ultrasonic vibration heating. In case of transient thermography, the heating is discontinued after the surface reaches a predefined temperature.

At step 404, the IR imaging device 102 captures a plurality of thermal images of the surface over a period of time. The IR imaging device 102 being triggered by the variable time base generator 108, captures the plurality of thermal images of the surface at non-linear intervals of time. Further, each of the thermal images is associated with temporal data generated by the time module 110. The plurality of thermal images and the associated temporal data may be stored in the frame buffer 104.

At step 406, the image processor 114 processes the plurality of thermal images and the temporal data. In one example implementation, the image processor 114 determines the contrast of each pixel by subtracting a mean intensity of all pixels of that thermal image from the pixel intensity at that point of time. The contrast is then plotted versus time for each pixel, using the temporal data associated with the thermal images.

At step 408, the image processor 114 identifies features within the object, based on the processing. The image processor 114 may estimate a depth of the feature based on the temporal data associated with a peak of the contrast plot. Such identification is particularly useful where the feature's thickness does not force the heat to flow around the feature (also known as a "through heat" feature).

However, when the rate of diffusion of the heat is faster around the feature than through the feature (also known as a "lateral heat" feature), the contrast peak is not evident from the contrast plot. In such a case, the processor 114 computes, at step 406, the time derivative of the contrast plot to determine the time derivative peak of contrast. Subsequently, at step 408, the processor 114 may identify the depth of the "lateral heat" feature based on the temporal data associated with the time derivative peak of contrast.

Although specific implementations have been described in the embodiments presented herein, such implementations are exemplary, and should not be considered limiting in scope. Other variations of the implementations are also envisioned and the scope is defined by the appended claims.

The invention claimed is:

1. A method comprising:
   storing a plurality of time base functions into a variable time base generator, wherein each time base function of the plurality of stored time base functions is associated with a specific composite material to be tested, and further wherein each of the time base functions is associated with a composite material that is different from the composite material associated with each other time base function;
   selecting a time base function from the plurality of stored time base functions;
   capturing via an infra-red imaging device, a plurality of thermal images of a surface of a composite material associated with the time base function at non-linear time intervals over a period of time defined by the time base function, wherein the non-linear time intervals increase with the passing of time during the time period;
   varying the non-linear time intervals in response to a thermal transient;
   generating via a time module, temporal data unique to each captured thermal image;
   processing via a processor, the plurality of thermal images and the temporal data together such that the temporal data associated with each captured thermal image directly relates to features within the composite material associated with the time base function; and
   identifying features within the composite material associated with the time base function based on the processing.

2. The method of claim 1, wherein the non-linear intervals are based on a step function of time, a square law function of time, or a combination thereof.

3. The method of claim 1, wherein the non-linear intervals are defined based on a function of thermal emissivity of the composite material.

4. The method of claim 1, wherein the non-linear intervals are defined based on an image processing function used in the processing of the plurality of thermal images.

5. A system comprising:
   an infra-red imaging device that captures a plurality of thermal images of a surface of a composite material;
   a variable time base generator comprising a plurality of time base functions stored therein, wherein each time base function of the plurality of stored time base functions is associated with a specific composite material to be tested, and further wherein each time base function is associated with a composite material that is different from the composite material associated with each other time base function, and further wherein the variable time base generator triggers the infra-red imaging device at non-linear time intervals over a period of time defined by a time base function selected from the plurality of stored time base functions, wherein the non-linear time intervals increase with the passing of time during the time period and varying the non-linear time intervals upon detection of a thermal transient;
   a time module that generates temporal data unique to each of the plurality of captured thermal images; and
   a processor that processes the plurality of captured thermal images and the temporal data together to identify features within the composite material associated with the time base function, wherein the temporal data associated with each captured thermal image directly relates to features within the composite material associated with the time base function.

6. The system of claim 5, further comprising a heater that heats the surface of the composite material.

7. The system of claim 6, wherein the heater includes one of a flash lamp, a quartz lamp, a microwave tube, or a laser source.

8. The system of claim 5, wherein the variable time base generator includes a step function generator, a square law function generator, or a combination thereof.

9. The system of claim 5, wherein the variable time base generator includes a programmable function generator comprising:
   an input that accepts a material selection;
   a memory unit that stores the plurality of time base functions, each of the plurality of time base functions corresponding to thermal emissivity of a specific material; and a selector that selects an appropriate one of the plurality of time base functions based on the input.

10. The system of claim 5, wherein the variable time base generator comprises a hard wired function generator.

11. The system of claim 5, wherein the infra red imaging device includes a focal plane array sensor.

12. The system of claim 5, wherein the time module associates a time stamp with each of the plurality of thermal images.

13. A computer program product comprising a non-transitory computer readable medium encoded with computer-executable instructions, wherein the computer executable instructions, when executed, cause one or more processors to:
   select one of a stored plurality of time base functions, wherein each time base function of the plurality of time base functions is associated with a specific composite material to be tested, and further wherein each time base function is associated with a composite material that is different from the composite material associated with each other time base function;
   trigger an infra-red imaging device to capture a plurality of thermal images of a surface of a composite material associated with the selected time base function at non-linear time intervals over a period of time defined by the selected time base function, wherein the non-linear time intervals increase with the passing of time during the time period and the non-linear time intervals are varied in response to detection of a thermal transient, each of the captured thermal images being associated with temporal data that is unique to the captured thermal image;
   receive the plurality of captured thermal images and the temporal data;
   process the plurality of captured thermal images and the temporal data together such that the temporal data associated with each captured thermal image directly relates to features within the composite material associated with the selected time base function; and identify features within the object based on the processing.

14. The computer program product of claim 13, wherein the non-linear intervals comprise a step function of time, or a square law function of time.

15. The computer program product of claim 13, wherein the non-linear intervals are defined based on a function of thermal emissivity of the composite material.

16. The computer program product of claim 13, wherein the non-linear intervals are defined based on an image processing function used in the processing of the plurality of thermal images.

17. The method of claim 1, wherein identifying features within the composite material based on the processing comprises identifying a depth of lateral heat based on temporal data associated with a time derivative peak of contrast plot.

18. The system of claim 5, wherein the processor further processes temporal data associated with a time derivative peak of contrast plot to identify a depth of lateral heat.

19. The computer program product of claim 13, wherein the computer-executable instructions, when executed, further cause the one or more processors to identify a depth of lateral heat within the composite material based on temporal data associated with a time derivative peak of contrast plot.

* * * * *